US00PP19719P2

(12) United States Plant Patent
Noodelijk

(10) Patent No.: US PP19,719 P2
(45) Date of Patent: Feb. 17, 2009

(54) *CHRYSANTHEMUM* PLANT NAMED 'FASNO YELLOW'

(50) Latin Name: *Chrysanthemum morifolium*
Varietal Denomination: Fasno Yellow

(76) Inventor: Robert Noodelijk, Vrouwgeestweg 26, Woubrugge (NL), 2481 KN ( * ) Notice: Subject to any disclaimer, the term of this patent is extended or adjusted under 35 U.S.C. 154(b) by 0 days.

(21) Appl. No.: 12/001,825

(22) Filed: Dec. 13, 2007

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent L Bell
(74) *Attorney, Agent, or Firm*—Jondle & Associates, P.C.

(57) ABSTRACT

A *chrysanthemum* plant named 'Fasno Yellow' characterized by small-sized blooms with yellow ray florets and prolific branching, a natural season flowering date of September 22, a blooming for a period of 6 weeks, a rounded plant habit and a spreading growth habit with a moderate growth rate, is disclosed.

1 Drawing Sheet

Genus: *Chrysanthemum morifolium.*
Variety denomination: 'Fasno Yellow'

BACKGROUND OF THE INVENTION

'Fasno Yellow' is a product of a breeding and selection program for outdoor pot mums (garden mums) which had the objective of creating new *chrysanthemum* cultivars with a decorative type inflorescence, a natural season blooming date around September 22 and a blooming period of 6 weeks. The new plant of the present invention comprises a new and distinct cultivar of *chrysanthemum* plant.

'Fasno Yellow' is a seedling resulting from the open pollination among groups of un-named, unpatented *chrysanthemum* cultivars maintained under the control of the inventor for breeding purposes. The new and distinct cultivar was discovered and selected as one flowering plant by Rob Noodelijk in a cultivated field in Woubrugge, The Netherlands in September 2005. The plant has been asexually reproduced by cuttings in greenhouses at Woubrugge, The Netherlands over a two year period. The new cultivar has been found to retain its distinctive characteristics through successive asexual propagations.

SUMMARY OF THE INVENTION

The following are the most outstanding and distinguishing characteristics of the new cultivar when grown under normal horticultural practices in Woubrugge, The Netherlands.

1. A rounded plant habit;
2. A spreading growth habit and moderate growth rate; and
3. Small, double, yellow inflorescences.

DESCRIPTION OF THE PHOTOGRAPHS

The present invention of a new and distinct variety of *chrysanthemum* is shown in the accompanying photographs, the colors being as nearly true as possible with color photographs of this type.

DESCRIPTION OF THE INVENTION

Figure 1:
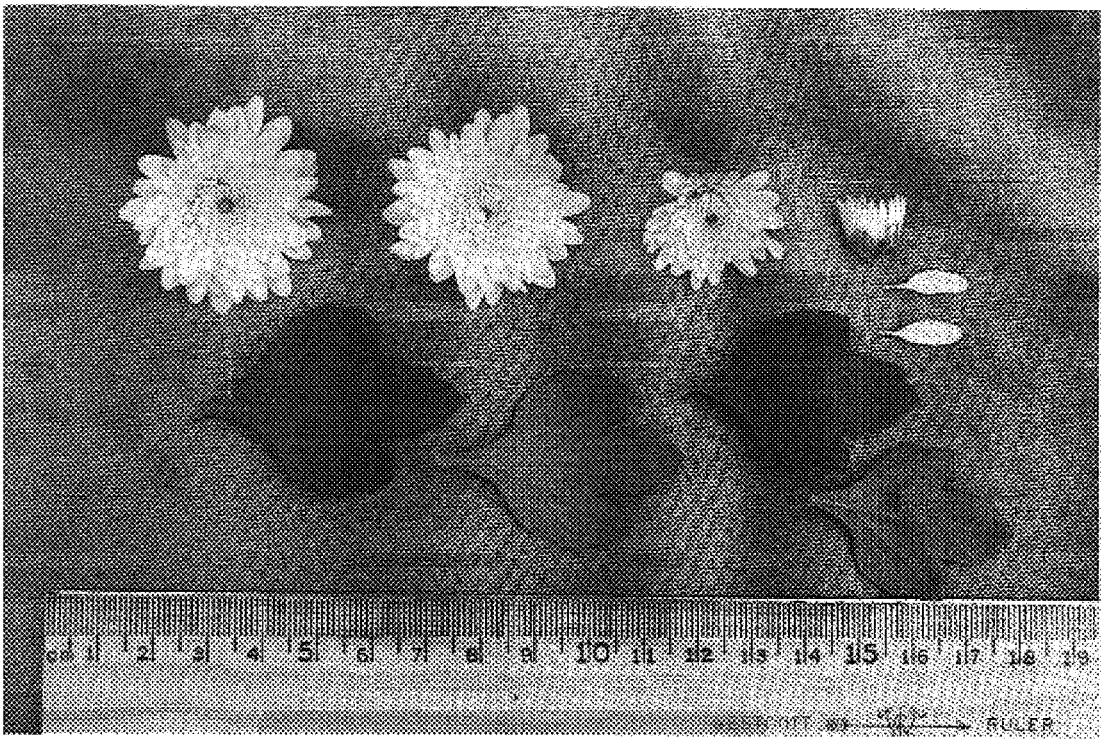
FIG. 1 shows a close-up of the individual inflorescences, florets, bud and leaves.
Figure 2:
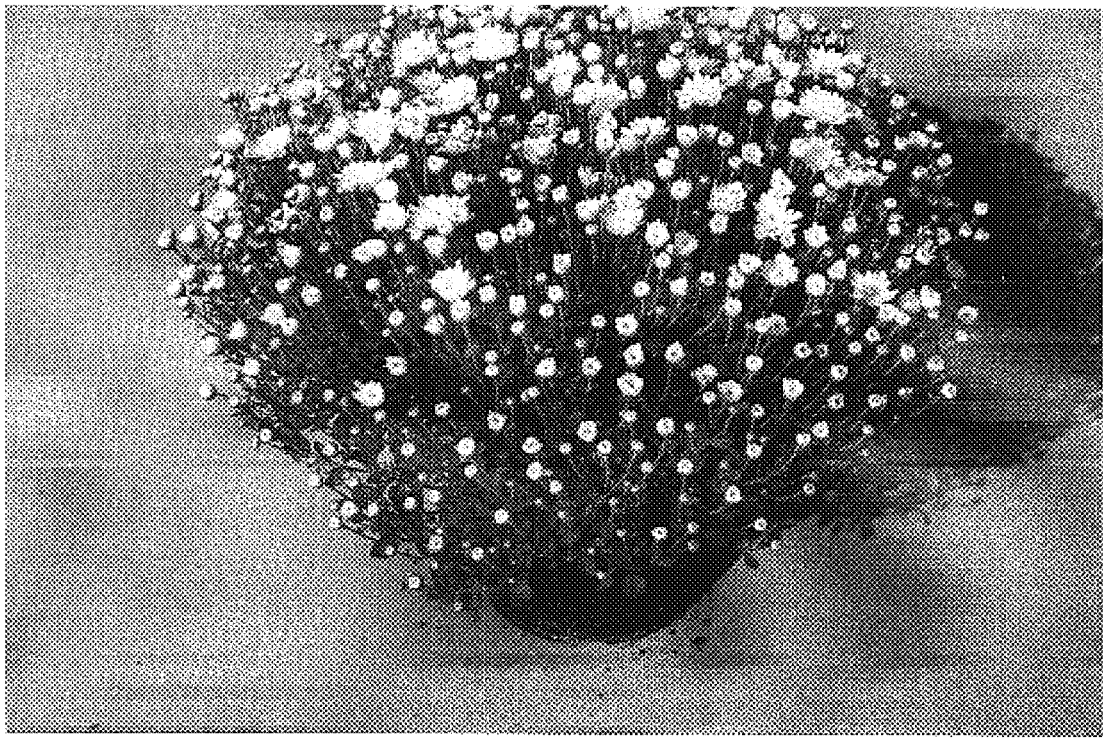
FIG. 2 shows a plant of the cultivar in full bloom.

This new variety of *chrysanthemum* is of the botanical classification *Chrysanthemum morifolium.* The observations and measurements were gathered from plants grown out door in Woubrugge, The Netherlands under natural day length and temperature and planted in week 22 in 2005 and 2006. The natural blooming date of this crop was September 22. The average height of the plants was 40 cm. No growth retardants were used. No tests were done on disease or insect resistance or susceptibility. No tests were done on cold or drought tolerance. This new variety produces small-sized blooms with yellow ray florets and yellow centers, blooming for a period of 6 weeks.

The following is a description of the plant and characteristics that distinguish 'Fasno Yellow' as a new and distinct variety. The color designations are taken from the plant itself. Accordingly, any discrepancies between the color designations and the colors depicted in the photographs are due to photographic tolerances. The color chart used in this description is The Royal Horticultural Society Colour Chart, edition 1995.

DETAILED BOTANICAL DESCRIPTION OF 'FASNO YELLOW'

Plant:
- *Shaped.*—Rounded.
- *Growth habit.*—Spreading.
- *Growth rate.*—Moderate.
- *Height.*—42 cm to 45 cm.
- *Width.*—45 cm.

Branches:
- *Stem.*—Color: RHS 137D (green). Strength: Strong. Brittleness: Absent. Anthocyanin coloration: Absent.
- *Length of lateral branch (from top to bottom).*—18 cm to 20 cm.

*Lateral branch color.*—RHS 137D (green).
*Lateral branch attachment.*—Petiolate.
*Branching* (*average number of lateral branches*).—Very prolific with 11 branches after pinching.

Leaves:
*Color.*—Upper surface: RHS 147A (yellow-green). Lower surface: RHS 147A (yellow-green).
*Size.*—General: Small. Length: 3.5 cm to 3.7 cm. Width: 3.5 cm to 3.7 cm.
*Quantity* (*number per lateral branch*).—5 to 6.
*Shape.*—Round.
*Apex.*—Acute.
*Base.*—Obtuse.
*Margin.*—Crenate (almost entire).
*Texture.*—Upper surface: Glabrous. Lower surface: Pubescent.
*Venation arrangement.*—Palmate.
*Shape of base of sinus between lateral lobes.*—Acute.
*Margin of sinus between lateral lobes.*—Diverging.

Bud:
*Size.*—General: Small. Cross-section: 1.2 cm. Height: 1.2 cm.
*Outside color.*—RHS 6A (yellow).
*Involucral bracts.*—2 rows, length 0.7 cm, width 0.3 cm.
*Involucral bracts among disc-florets.*—Absent.
*Involucral bracts color.*—RHS 138B (green).

Bloom:
*Type.*—Double.
*Size.*—General: Small. Fully expanded: 3.8 cm to 4.2 cm.
*Number of blooms per branch.*—Approximately 5 to 7 blooms per branch.
*Performance on the plant* (*blooming period*).—6 weeks.
*Fragrance.*—Typical *chrysanthemum*; slight.
*Tonality from distance.*—A very rich flowering garden mum with small yellow inflorescences.
*Discoloration to color.*—None.
*Peduncle.*—Length: 7 cm to 10 cm. Color: RHS 137D (green).
*Natural season blooming date.*—22 September.

Ray florets:
*Texture.*—Both the upper and lower surfaces are smooth.
*Number.*—130 to 150.
*Cross-section.*—Flat.
*Longitudinal axis of majority.*—Flat to reflexing.
*Length of corolla tube.*—0.2 cm to 0.3 cm.
*Apex.*—Round.
*Margin.*—Entire.
*Length.*—2.9 cm to 3.1 cm.
*Width.*—1.0 cm to 1.2 cm.
*Color.*—Upper surface of the outer ray-florets: RHS 7A (yellow).
*Lower surface.*—RHS 6B (yellow).
*Ratio length/width.*—Medium.

Disc florets:
*Center of the flower* (*disc-florets*).—Immature: RHS 146B (yellow-green). Mature: RHS 146B (yellow-green).
*Disc floret.*—Present.
*Disc diameter.*—0.3 cm to 0.4 cm.
*Disc length.*—0.6 cm.
*Distribution of disc florets.*—A few, visible at all stages of flowering.
*Shape.*—Funnel-shaped.
*Color.*—RHS 144A (yellow-green).
*Receptacle shape.*—Domed flat.

Reproductive organs:
*Stamen* (*present in disc florets only*).—Absent.
*Pollen.*—Absent.
*Styles.*—Thin.
*Style color.*—RHS 144A (yellow-green).
*Style length.*—0.3 cm.
*Stigmas color.*—RHS 144A (yellow-green).
*Stigma width.*—0.1 cm.
*Ovaries.*—Enclosed in calyx.

Fruit/Seed set: Seeds are produced in small quantities; ovate, RHS 199A (grey-brown) and 0.15 cm in length.

COMPARISON WITH COMMERCIAL CULTIVARS

'Fasno Yellow' differs from the commercial cutivar 'Yodawn' (U.S. Plant Pat. No. 17,452) in that 'Fasno Yellow' has a later flowering date (September 22) than 'Yodawn' (September 11). Additionally, 'Fasno Yellow' has narrow and tall ray florets, while 'Yodawn' has broader and rounder ray florets.

I claim:

1. A new and distinct variety of *chrysanthemum* plant as described and illustrated.

* * * * *